United States Patent [19]

Blanchard

[11] Patent Number: 4,883,481
[45] Date of Patent: Nov. 28, 1989

[54] ADJUSTABLE DISPOSABLE PANTY

[76] Inventor: JoAnn Blanchard, Apt. 101, 1423 Yonge St., Toronto, Ontario, Canada, K1P 5W6

[21] Appl. No.: 242,225

[22] Filed: Sep. 9, 1988

[51] Int. Cl.[4] .................... A41B 9/00; A41B 9/12
[52] U.S. Cl. .................. 604/385.1; 604/389; 604/385.2; 2/402; 2/403; 2/406
[58] Field of Search ............... 2/406, 403, 402; 604/367, 358, 386, 389, 391, 385.1, 385.2, 389

[56] References Cited

U.S. PATENT DOCUMENTS

| 2,427,906 | 9/1947 | Golightly et al. | 2/49 R |
|---|---|---|---|
| 2,632,177 | 3/1953 | McFerin | 2/406 |
| 2,834,347 | 5/1958 | Connally | 604/389 |
| 3,650,273 | 3/1972 | Schaar . | |
| 3,882,871 | 5/1975 | Taniguchi | 604/391 X |
| 3,916,900 | 11/1975 | Breyer et al. | 604/389 X |
| 4,051,854 | 10/1977 | Aaron | 2/DIG. 6 |
| 4,695,279 | 9/1987 | Steer | 2/406 X |
| 4,698,855 | 10/1987 | Hicks | 604/367 |
| 4,701,174 | 10/1987 | Johnson | 604/367 X |

Primary Examiner—Werner H. Schroeder
Assistant Examiner—Jeannette E. Chapman
Attorney, Agent, or Firm—David J. French

[57] ABSTRACT

An under garment is provided with size adjustment means for the waist-band in the form of a frangible tab that holds a pleat closed, but permits expansion of the pleat when broken. A tampon is also provided which has gore formed within the rear end portion so as to provide a more intimate fit over the buttocks of a wearer.

1 Claim, 6 Drawing Sheets

ADJUSTABLE DISPOSABLE PANTY

FIELD OF INVENTION

This invention relates to an undergarment adapted to be worn by adults. More particularly, this invention relates to a low-cost, disposable panty that is adaptable to fit persons of varying sizes, and is capable of carrying absorbant pads that are comfortable to wear.

BACKGROUND OF THE INVENTION

The use of disposable diapers for children and incontinent persons is now well established in the market. To date, however, there has been little success in popularizing a low-cost disposable panty for adults.

The disposable panty market is potentially substantial. It would appeal to persons who are away from home, travelling, and to persons who are fastidious about having clean underwear. But to establish such a market, a panty would have to be produced at very low cost.

A difficulty in endeavoring to serve a mass market for this line of product is the variability of size requirements of individuals. In order to fit persons of varying waist measurements, while still keeping cost down, it would be desirable to have a panty that is adaptable to fit various sizes of persons. This feature should be available again without increasing substantially the cost of the product.

While the introduction of a low-cost disposable panty could serve a very broad market, there is also a market for a combination panty and tampon. Such a product would meet the needs of women as they experience their monthly menstrual cycle.

A panty adapted for this market should combine absorbency potential with non-obtrusiveness. This requires that compromises be made in the quantity of absorbent material incorporated to function as a tampon. It further requires that care be taken in selecting the shape of the tampon in relation to the portion of the body over which it is intended to lie.

In the prior art, adhesive tapes have been used to gather the waist-line of panties to provide size control. An example in this category is U.S. Pat. No. 2,834,347 to Connally. The use of such tape is, however, limited by the strength of the adhesive. Further, the gathered portion of an adhesively held waistband will be ruffled in a disorganized manner.

In the area of absorbent pads, patents such as U.S. 4,229,835 to Shaw and 4,642,110 to Dudek depict examples of pads incorporated into an undergarment or diaper. Shaw depicts an absorbent pad that is limited in coverage to the crotch. Dudek shows an absorbent pad that extends from the front to the rear waistband region, and incorporates a series of "V"-shaped notches to aid in gathering of the pad around the waist. U.S. Pat. No. 2,749,556 to Lampkowitz shows an adjustable waistband in which folded pleats are provided to provide material for the waistband to expand. A similar feature appears in Zins, U.S. Pat. No. 3,097,365.

SUMMARY OF THE INVENTION

Accordingly, this invention comprises in one aspect a panty with an adjustable waistband, such waistband having at least one pleat formed therein, and a frangible tab adapted to hold such pleat closed and capable of being broken so as to permit the expansion of such pleat.

By a further feature of the invention consecutive pleats held closed by frangible tabs may be incorporated one beneath the other whereby a progressive enlargement of the waistband of the panty may be obtained by progressively breaking such tabs.

By a further feature of the invention a moisture-absorbing tampon is disclosed which may be incorporated within the crotch region of said panties with such tampon extending rearwardly and upwardly over the buttocks, in the vicinity of the sacrum region of the back, such tampon being formed with a terminal central gore which adapts the tampon to fit against the central rear surface of the lower backside of a wearer, above the buttocks.

By a further feature of the invention at least a portion of the leg-enveloping edges of the panty are fitted with an elasticized draw cord which may be locked in position, thereby providing an assured tight fit for the panty around the leg opening.

These and further features of the invention will be apparent from the description of the preferred embodiments thereof described hereafter.

DESCRIPTION OF THE PREFERRED EMBODIMENTS

Figure 1:
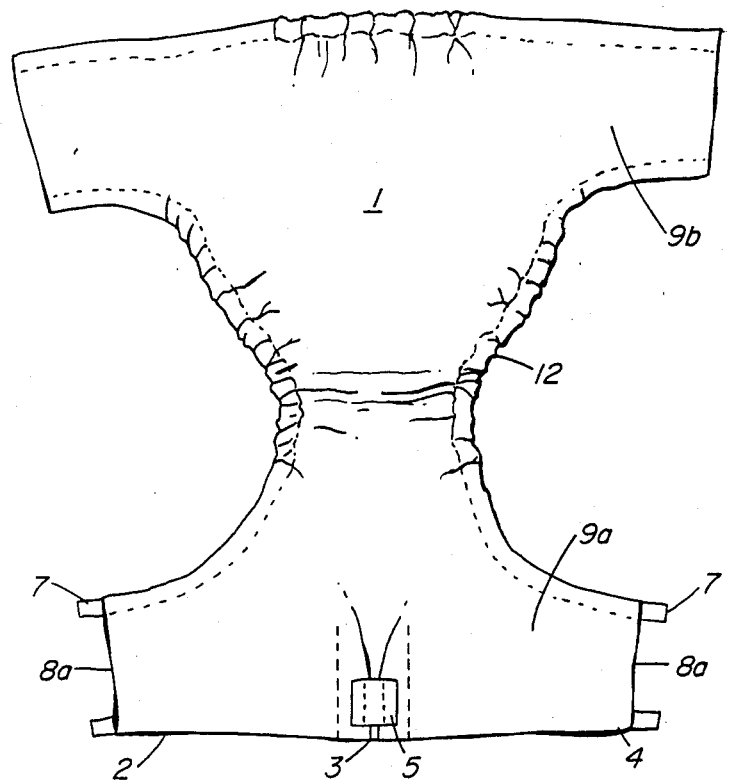
FIG. 1 is a view of a simple panty incorporating a pleat accordinng to the invention, with the panty laid-out flat prior to being placed on a wearer.

In FIG. 1 a pattern for a panty is cut from a suitable fabric or sheeting material. This may be of polyurethane film or it may be of a non-woven or paper material, or other equivalent.

Figure 2:
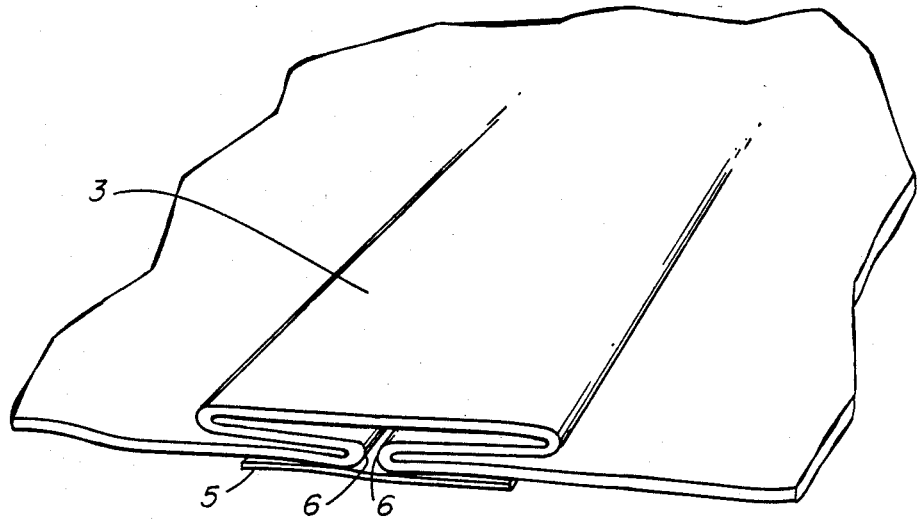
FIG. 2 is an enlarged view of the pleat, as viewed from the reverse, interior side of the panty as depicted in FIG. 1.
Figure 2A:
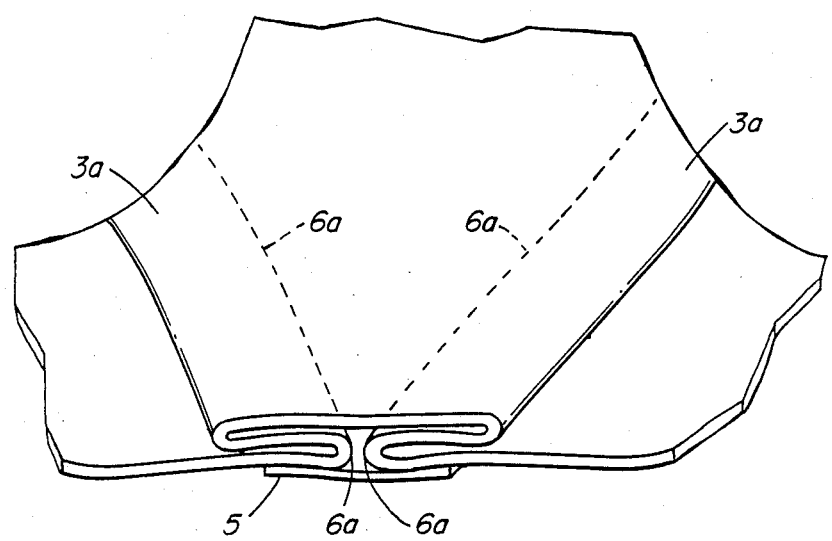
FIG. 2a depicts an alternate accordian-like pleat.

At the front end 2 of the diaper 1, a pleat 3 is formed in the waistband edge 4. This may be a simple double folded run-out pleat best seen in end view in FIG. 2. This form of pleat disappears into a gathering of the fabric. An alternate form of pleat 3a shown in FIG. 2a is akin to an accordian fold. This latter configuration embodies fold lines that extend to the leg opening and avoids forming a bulge or distortion in the panty sheeting. The pleat 3, in either case, is held closed by a frangible break-away tab 5.

The tab 5 is preferably of a paper or plastic material that can be bonded by an adhesive, by stitching or by welding to the diaper, along or next to the inner folded edges 6, 6a of the pleat 3, 3a. It is of such dimensions and is so positioned as to hold the pleat edges 6, 6a close together, thereby providing a waistband edge 4 of reduced length. When the tab 5 is broken, the pleat 3, 3a can expand, and the waist-band edge 4 of the panty may extend to its maximum dimension.

By this feature the size of waist that the panty can accommodate is readily changeable.

Figure 3:
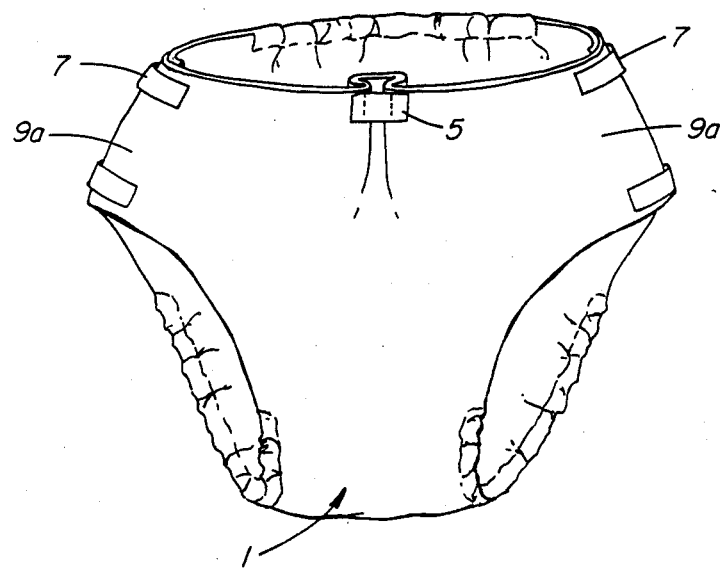
FIG. 3 is a view of the panty from the front, as assembled on a wearer.

The panty may be assembled by the wearer by forming it into the shape depicted in FIG. 3. Pressure sensitive adhesive tabs 7 along the ends 8a, of the front side panels 9a of the panty 1 allow the panty to be secured in position by attachment to the rear side panels 9b. While a degree of adjustability is inherent in the provision of the adhesive tabs 7, the break-away tab 5 provides a substantial degree of adjustment with greatly enhances the adaptability of panties made in accordance with the invention.

Figure 4:
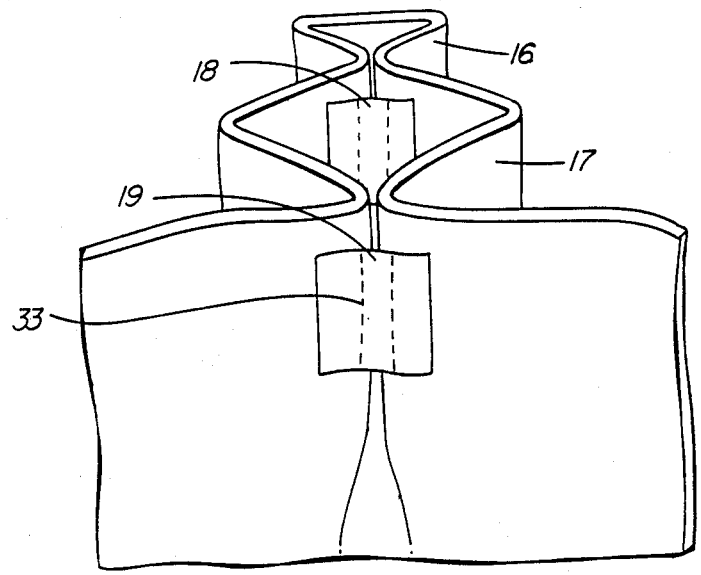
FIG. 4 is a schematic view of a composite pleat containing two break-away tabs.
Figure 4A:
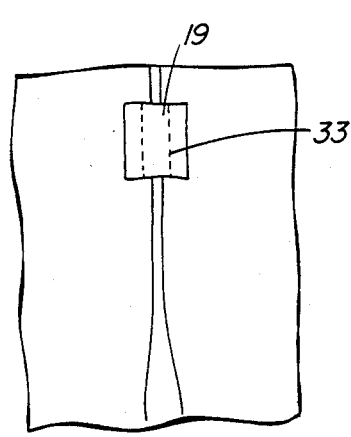
FIGS. 4a, 4b and 4c show the progressive effects of rupturing the break-away tabs shown in FIG. 4.
Figure 4B:
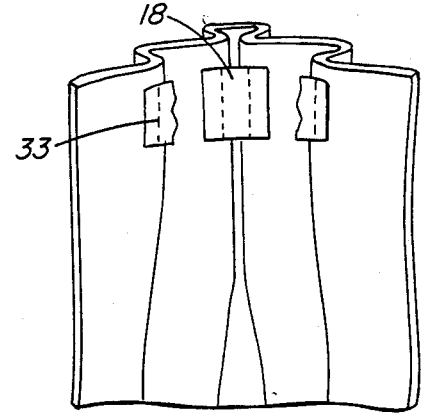
Figure 4C:
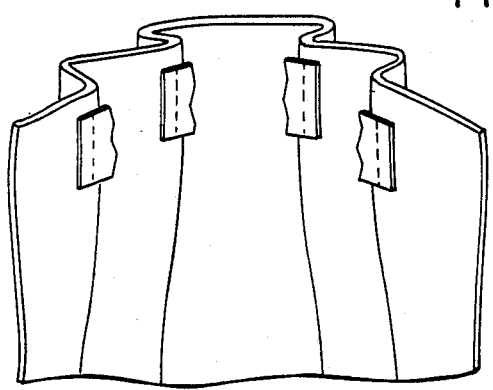

The feature of a pleat with breakaway tab may be super-imposed on itself so as to incorporate several stages of adjustment. FIG. 4 shows two super-imposed pleats in which an inner pleat 16 is formed within or beneath the material of an outer pleat 17. Again, breakaway tabs 18, 19 are provided so as to permit progressive adjustment of the waistband size. This is depicted in FIGS. 4a, 4b, 4c with stitching 33 shown as the means for attaching the break-away tabs 18, 19.

Figure 5:
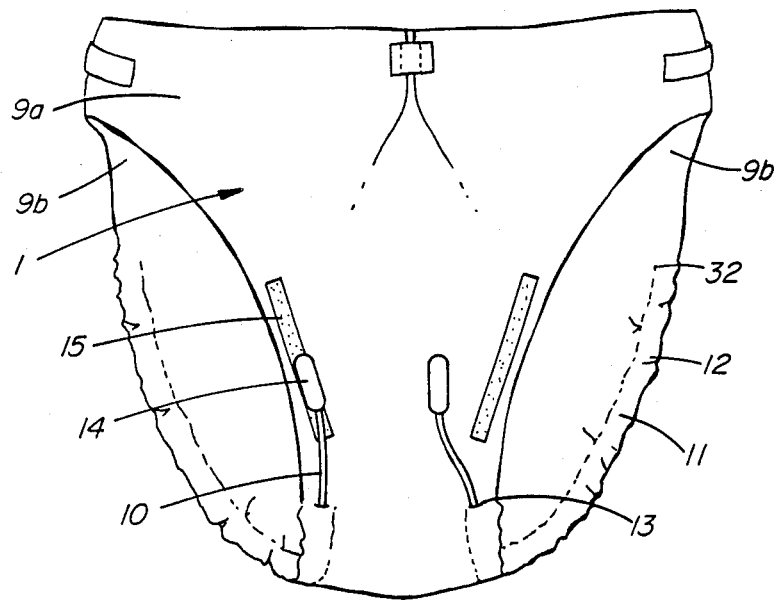
FIG. 5 shows the drawstring on a panty from the front view.

Another feature of the invention is a drawstring 10 that is contained within a sleeve 11, along the edge of the leg-opening portion 12 of the panty 1. While such strings are known, FIG. 5 depicts a feature which allows the tension in the drawstring 10 to be adjusted with great convenience.

The string 10 is anchored at the rear end 32 of the sleeve 11, at the edge of the rear panel 9b. This may conveniently be done by use of an adhesive, by stitching or by other appropriate means.

At the front end 13 of the sleeve 11, the drawstring 10 emerges in the region adjacent to the front side panel 9a whereby a wearer may have easy access thereto. The string 10, as shown in FIG. 5, is provided with an attachment means, such as a pad 14 of the VELCRO-brand type which may be anchored on a complementary attachment strip 15 at various positions. This provides a means for controlling the tightness of the closure of the leg opening. Optionally the draw-string 10 may be of limited elasticity to improve the comfort of fit of the leg opening. A slight degree of elasticity will provide foregiveness when the string is stretched, as where the wearer flexes their muscles while walking.

The panty as so far described is intended to be a low cost product of universal application. It may be worn by men, women or children. In the case of persons of greatly differing sizes, it may be appropriate to provide special size categories. But within each category, the break-away tab and locking drawstring features will provide individual adaptability to the waist and leg dimensions of the wearer.

The panty of the invention may also be adapted to carry a feminine tampon for absorbing a woman's menstrual flow. It may further be adapted to provide protection for persons suffering from moderate incontinence or lack of bladder control.

Figure 6:
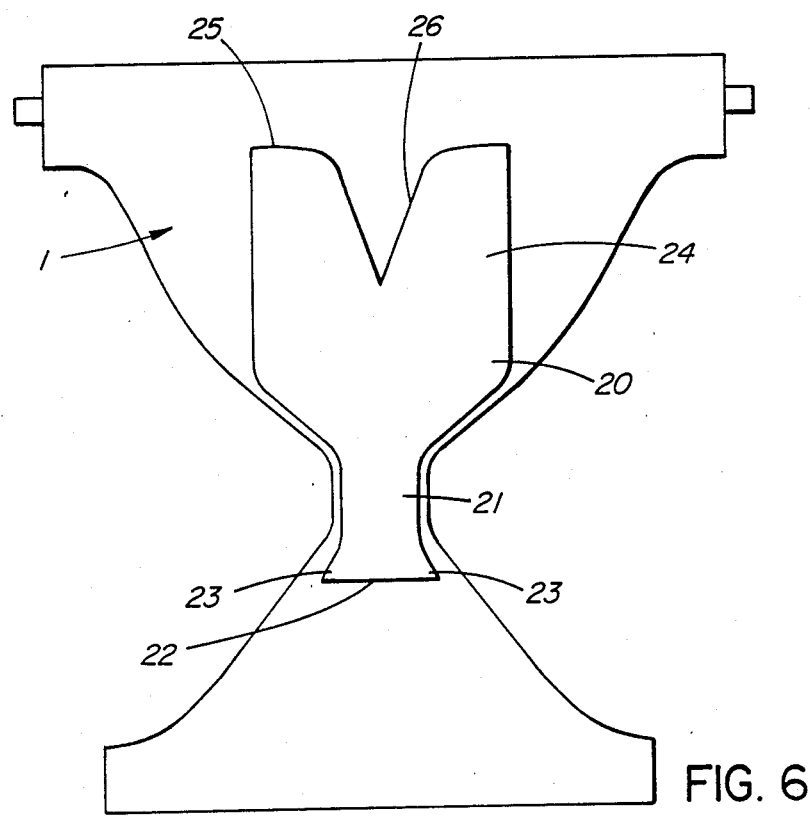
FIG. 6 shows a panty with the specially-shaped absorbent pad in position.

A tampon adapted to be installed within a panty 1 of the invention is shown in FIG. 6. This tampon 20 is formed with a narrowed central crotch region 21 that opens in its forward end 22 with a slightly fanned portion 23. This fanned portion 23 serves to stabilize the tampon 20 within the crotch region of a wearer and keep it from shifting position.

The rearward portion 24 of the tampon 20 extends further from the narrowed central crotch region 21 than the forward end 22. This rearward portion 24 is therefore capable of extending substantially up over the buttocks region. The rearward end 25 of the rearward position 24 of the tampon 20 terminates short of the waistband level of the panty. Along its terminating end 25 is a gore 26.

The purpose of the gore 26 is to allow the rearward portion 24 of the tampon 20 to conform more nearly to the shape of the buttocks, and particularly to the shape of the sacrum region of the back. The gore 26 is depicted as "V" shaped. It need not be precisely in the form of a "V" with straight sides but may be shaped with edges which nearly close, but normally do not overlap, when in position on a wearer.

Figure 7:
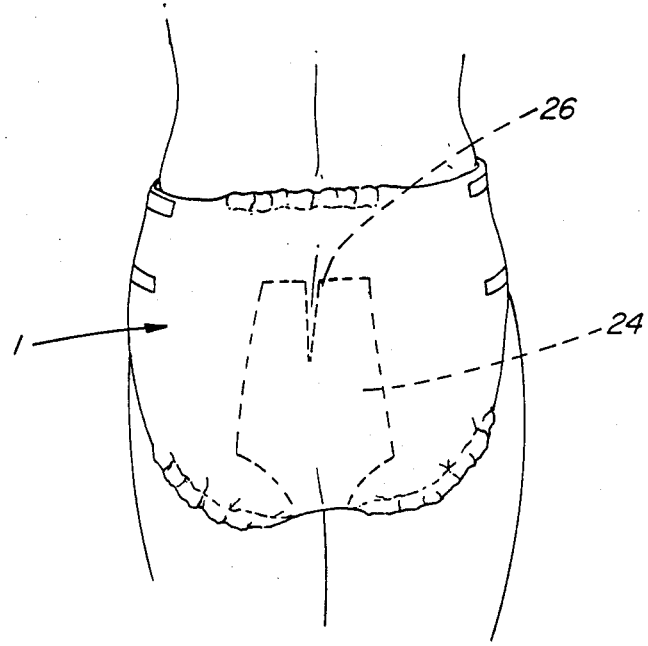
FIG. 7 shows the positioning of the absorbent pad on the wearer.

The rearward portion 24 of the tampon 20 should not be unduly wide as its thickness will inconvenience the wearer if it extends substantially beyond either side of the centre of the buttocks. This portion 24 will, however, fit comfortably against the sacrum region of the back, against the buttocks, as shown in FIG. 7.

The tampon 20 is intended to be of moderate thickness so as not to protrude excessively from within the panty. To accommodate women experiencing a heavy menstrual flow a further central absorbent pad 27 may also be added in the crotch region.

Figure 8:
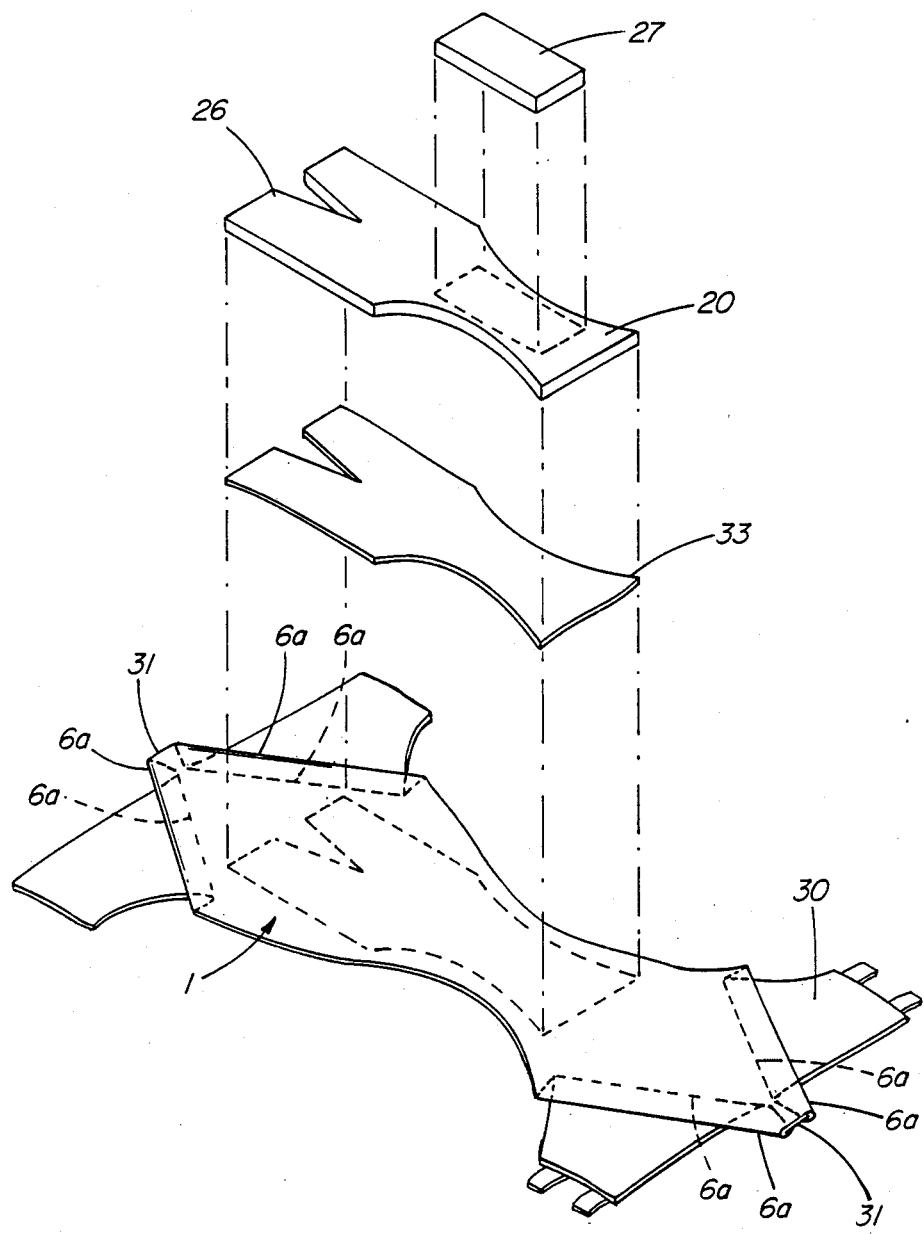
FIG. 8 shows an exploded assembly drawing for the panty with absorbent pad.

FIG. 8 shows an exploded composite of the assembly of these elements of an absorbent panty, according to the invention. The panty 1 is shown with the pleat fold lines 6a of the type of FIG. 2a formed therein at both front and rear. The exterior sheeting 30 will naturally thereby form an extra protruding trapezoid 31 of material. These may be cutoff to give the appearance of linearity to the waistband before the breakaway tabs 5 are ruptured (as in FIG. 2a), or may be left on to provide such an appearance once the breakaway tabs 5 are broken.

It is appropriate to form the external sheeting 30 from an impermeable material, such as polyurethane film, or the equivalent. In such a case, a fine gauze-like fabric may be bonded to the inner surface of the external sheeting 30 to provide a comfortable tactile surface next to the skin.

As a further feature to restrain the migration of moisture, an impermeable sheet 33, made of a material such as polyurethane, may be interposed between the tampon 20, and the gauze-covered sheeting 30 and fastened in place by adhesives. the absorbent tampon 20 with the gore 26 may be fastened to this sheet in turn by adhesives, followed by the final central absorbent pad 27, similarly attached.

By incorporating the features and special adaptations for fit and comfort as described into a panty, made in accordance to the invention, an improved product of potential mass appeal may be produced. The features disclosed all contribute to minimizing the cost of the product while providing user comfort in terms of both fit and appearance.

The foregoing comprises a description of preferred embodiments of the invention in its various aspects. The invention in its broadest and more detailed aspects is further described and defined by the claims which now follow.

The embodiments of the invention in which an exclusive property or privilege is claimed are defined as follows:

1. A human undergarment in the form of a panty formed of a flexible sheeting material and having a waistband region and a central crotch-covering region wherein a first pleat is formed of said waistband region, said first pleat being held closed by a frangible tab, and wherein a second pleat held closed by a frangible tab is formed within said first pleat.

* * * * *